United States Patent
Grunewald

(10) Patent No.: US 8,498,686 B2
(45) Date of Patent: Jul. 30, 2013

(54) MAPPING CATHETER WITH SPIRAL ELECTRODE ASSEMBLY

(75) Inventor: Debby Grunewald, Los Angeles, CA (US)

(73) Assignee: Biosense Webster (Israel), Ltd., Yokneam (IL)

( * ) Notice: Subject to any disclaimer, the term of this patent is extended or adjusted under 35 U.S.C. 154(b) by 0 days.

(21) Appl. No.: 13/252,891

(22) Filed: Oct. 4, 2011

(65) Prior Publication Data
US 2013/0085360 A1   Apr. 4, 2013

(51) Int. Cl.
*A61B 5/042* (2006.01)
(52) U.S. Cl.
USPC .......................................................... 600/374
(58) Field of Classification Search
USPC .......................................................... 600/374
See application file for complete search history.

(56) References Cited

U.S. PATENT DOCUMENTS

| | | | |
|---|---|---|---|
| 5,239,999 A * | 8/1993 | Imran | 600/374 |
| 5,297,549 A | 3/1994 | Beatty et al. | |
| 5,311,866 A | 5/1994 | Kagan et al. | |
| 5,385,146 A | 1/1995 | Goldreyer | |
| 5,406,946 A | 4/1995 | Imran | |
| 5,450,846 A | 9/1995 | Goldreyer | |
| 5,487,391 A | 1/1996 | Panescu | |
| 5,546,951 A | 8/1996 | Ben-Haim | |
| 5,662,108 A | 9/1997 | Budd et al. | |
| 5,680,860 A | 10/1997 | Imran | |
| 5,738,096 A | 4/1998 | Ben-Haim | |
| 5,772,590 A * | 6/1998 | Webster, Jr. | 600/374 |
| 5,848,972 A | 12/1998 | Triedman et al. | |
| 5,938,694 A | 8/1999 | Jaraczewski et al. | |
| 5,964,757 A | 10/1999 | Ponzi | |
| 6,024,739 A | 2/2000 | Ponzi et al. | |
| 6,163,716 A | 12/2000 | Edwards et al. | |
| 6,226,542 B1 | 5/2001 | Reisfeld | |
| 6,241,665 B1 | 6/2001 | Negus et al. | |
| 6,301,496 B1 | 10/2001 | Reisfeld | |
| 6,322,559 B1 * | 11/2001 | Daulton et al. | 606/41 |
| 6,430,426 B2 | 8/2002 | Avitall | |
| 6,628,976 B1 * | 9/2003 | Fuimaono et al. | 600/374 |
| 6,690,963 B2 | 2/2004 | Ben-Haim et al. | |

(Continued)

FOREIGN PATENT DOCUMENTS

| | | |
|---|---|---|
| EP | 2 269 505 A1 | 1/2011 |
| WO | WO 96/05768 | 2/1996 |
| WO | WO 97/17892 A1 | 5/1997 |
| WO | WO 03/089997 A2 | 10/2003 |

OTHER PUBLICATIONS

EPO Extended European Search Report for Application No. EP12187072.9, dated Feb. 18, 2013, 6 pgs.

*Primary Examiner* — Lee S Cohen
(74) *Attorney, Agent, or Firm* — Christie, Parker & Hale, LLP

(57) ABSTRACT

A mapping catheter adapted for use in a heart chamber, has a distal mapping assembly with a spiral ribbon that is radially expandable and contractable by means of an expander so that electrodes on the ribbon can contact heart wall at a plurality of locations simultaneously. The expander extends the length of the catheter between a control handle and a distal end of the spiral ribbon. The expander can be controlled directly at its proximal end by a user or the expander can be responsive to a puller wire controlled by a user interface on the control handle.

17 Claims, 17 Drawing Sheets

U.S. PATENT DOCUMENTS

| | | |
|---|---|---|
| 7,149,563 B2 * | 12/2006 | Fuimaono et al. ............ 600/374 |
| 7,255,695 B2 | 8/2007 | Falwell et al. |
| 7,850,685 B2 * | 12/2010 | Kunis et al. .................... 606/41 |
| 2005/0033136 A1 * | 2/2005 | Govari et al. ................. 600/374 |
| 2005/0222563 A1 | 10/2005 | McDaniel et al. |
| 2011/0054287 A1 | 3/2011 | Schultz |
| 2011/0054446 A1 | 3/2011 | Schultz |

\* cited by examiner

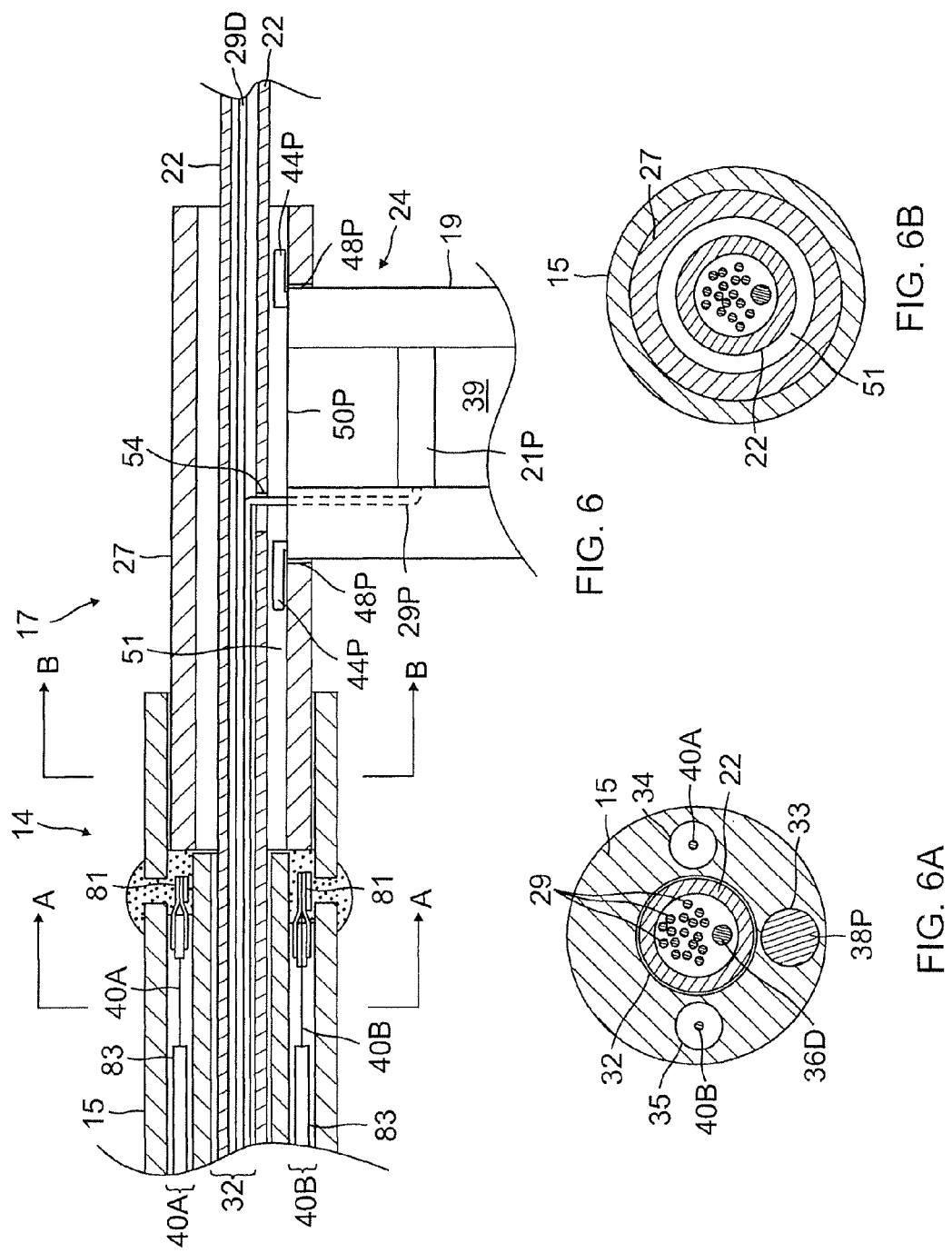

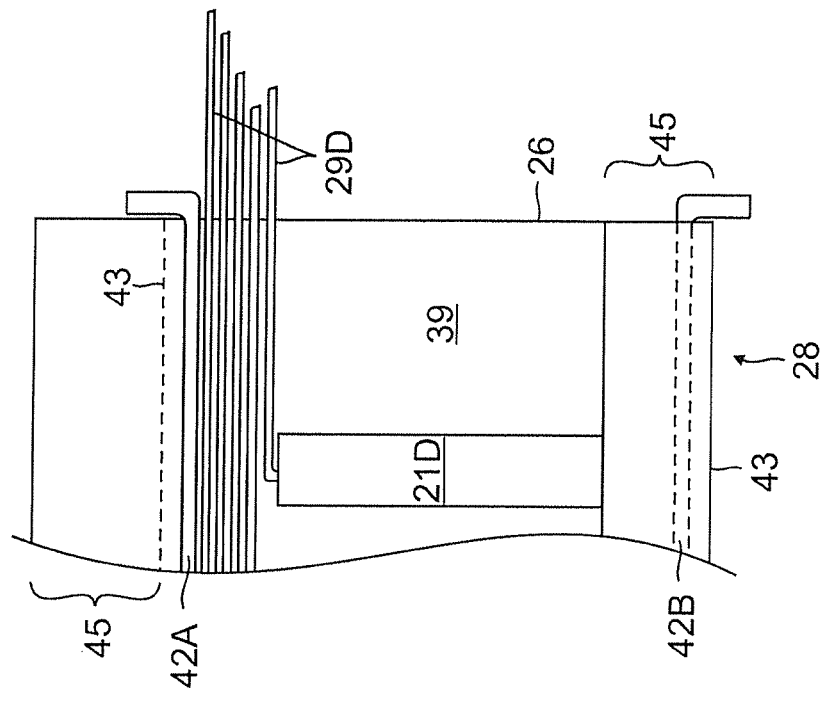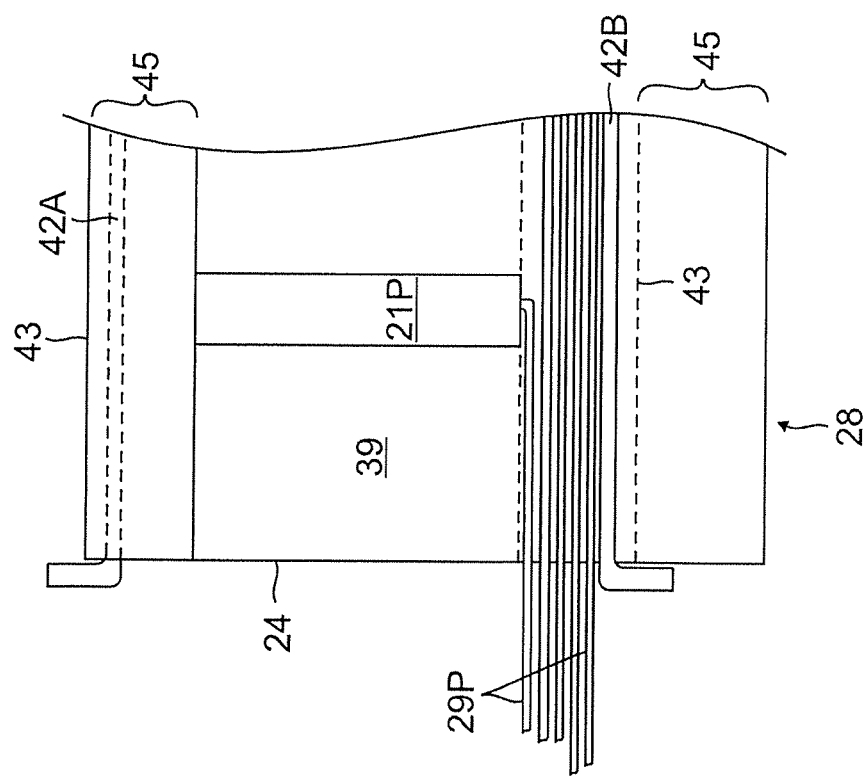
FIG. 7

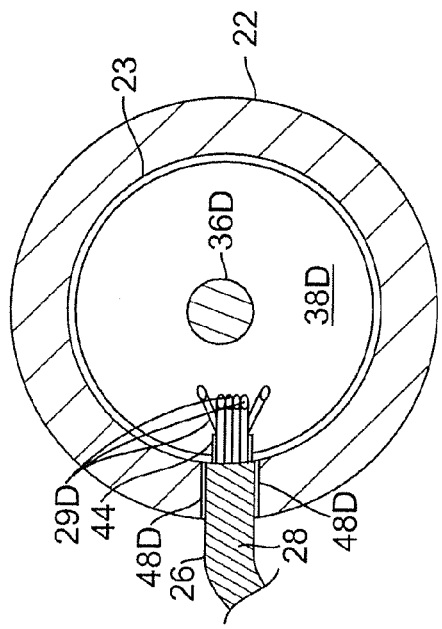
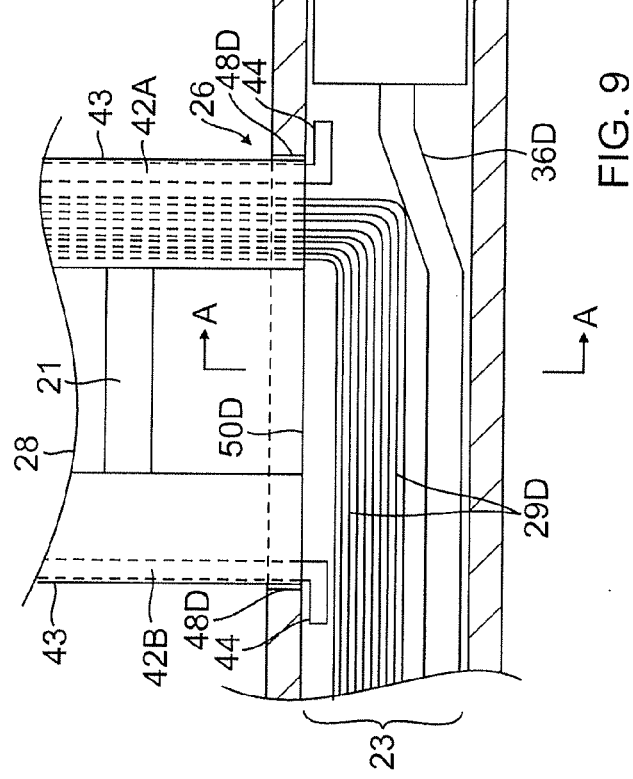
FIG. 9A
FIG. 9

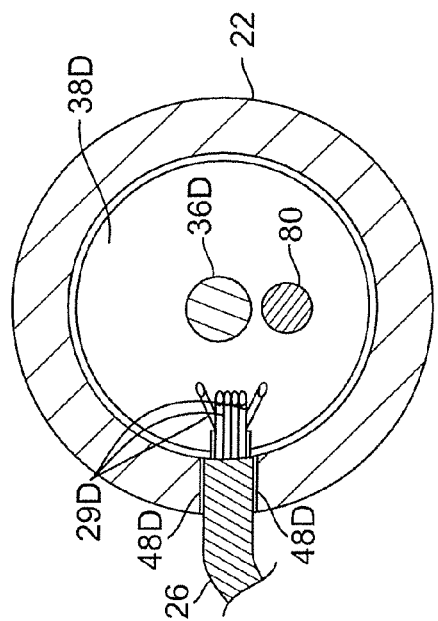
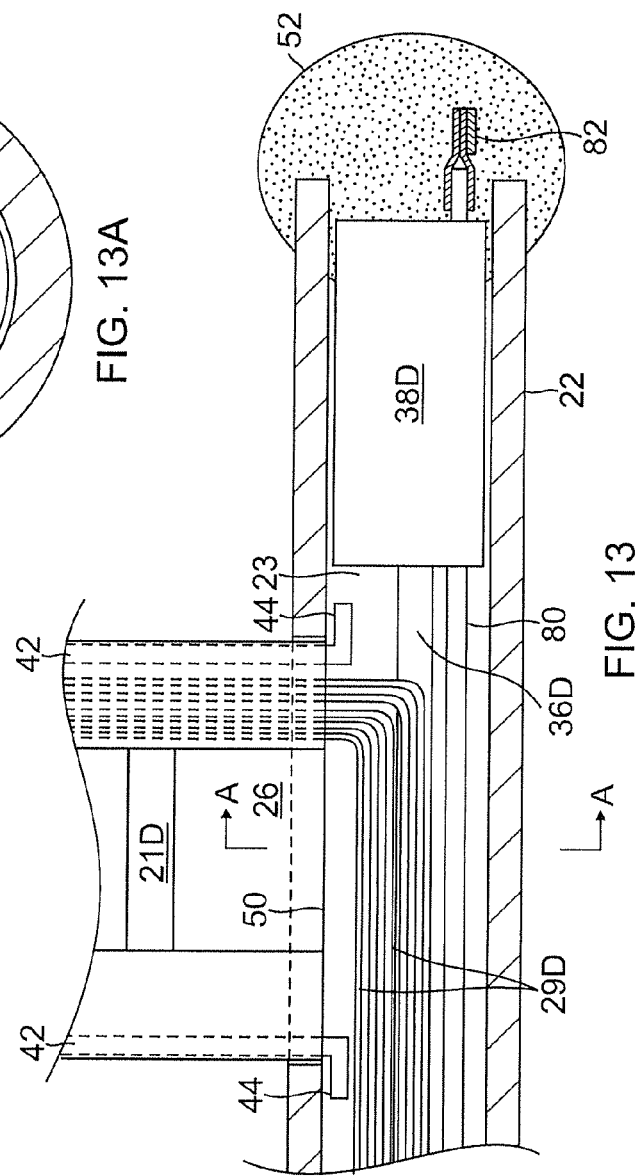
FIG. 13A
FIG. 13

MAPPING CATHETER WITH SPIRAL ELECTRODE ASSEMBLY

FIELD OF INVENTION

The invention is directed to catheters for rapidly generating an electrical map of a chamber of a heart utilizing an assembly of contact electrodes for obtaining information indicative of chamber electrical activity, and optionally, of chamber geometry.

BACKGROUND

Cardiac arrhythmias, the most common of which is ventricular tachycardia (VT), are a leading cause of death. In a majority of patients, VT originates from a 1 mm to 2 mm lesion located close to the inner surface of the heart chamber. One of the treatments for VT comprises mapping the electrical pathways of the heart to locate the lesion followed by ablation of the active site.

Commonly assigned U.S. Pat. No. 5,546,951; U.S. patent application Ser. No. 08/793,371; and PCT application WO 96/05768, which are incorporated herein in their entirety by reference, disclose methods for sensing an electrical property of heart tissue, for example, local activation time, as a function of the precise location within the heart. The data are acquired with one or more catheters that are advanced into the heart using catheters that have electrical and location sensors in their distal tips. Methods of creating a map of the electrical activity of the heart based on these data are disclosed in commonly assigned U.S. patent application Ser. Nos. 09/122, 137 and 09/357,559 filed on Jul. 24, 1998 and Jul. 22, 1999, respectively, which are also incorporated herein in their entirety by reference. As indicated in these applications, location and electrical activity is preferably initially measured on about 10 to about 20 points on the interior surface of the heart. These data points are then generally sufficient to generate a preliminary reconstruction or map of the cardiac surface to a satisfactory quality. The preliminary map is often combined with data taken at additional points in order to generate a more comprehensive map of the heart's electrical activity. In clinical settings, it is not uncommon to accumulate data at 100 or more sites to generate a detailed, comprehensive map of heart chamber electrical activity. The generated detailed map may then serve as the basis for deciding on a therapeutic course of action, for example, tissue ablation, to alter the propagation of the heart's electrical activity and to restore normal heart rhythm.

Catheters containing position sensors may be used to determine the trajectory of points on the cardiac surface. These trajectories may be used to infer motion characteristics such as the contractility of the tissue. As disclosed in U.S. Pat. No. 5,738,096 which is incorporated herein in its entirety by reference, maps depicting such motion characteristics may be constructed when the trajectory information is sampled at a sufficient number of points in the heart.

Electrical activity at a point in the heart is typically measured by advancing a catheter containing an electrical sensor at or near its distal tip to that point in the heart, contacting the tissue with the sensor and acquiring data at that point. One drawback with mapping a cardiac chamber using a catheter containing only a single, distal tip electrode is the long period of time required to accumulate data on a point-by-point basis over the requisite number of points required for a detailed map of the chamber as a whole. Accordingly, multiple-electrode catheters have been developed to simultaneously measure electrical activity at multiple points in the heart chamber.

U.S. Pat. No. 5,487,391, directed to systems and methods for deriving and displaying the propagation velocities of electrical events in the heart, is illustrative of contact methods found in the art. In the system disclosed in the '391 patent, the electrical probe is a three-dimensional structure that takes the form of a basket. In the illustrated embodiment, the basket is composed of 8 spines, each of which carries eight electrodes, for a total of 64 electrodes in the probe. The basket structure is designed such that when deployed, its electrodes are held in intimate contact against the endocardial surface.

U.S. Pat. No. 5,848,972 to Triedman et al. discloses a method for endocardial activation mapping using a multi-electrode catheter. In the method of the '972 patent, a multi-electrode catheter, preferably, a 50-electrode Webster-Jenkins™ basket catheter from Cordis-Webster of Baldwin Park, Calif., is advanced into a chamber of the heart. Anteroposterior (AP) and lateral fluorograms are obtained to establish the position and orientation of each of the electrodes. Electrograms are recorded from each of the electrodes in contact with the cardiac surface relative to a temporal reference such as the onset of the P-wave in sinus rhythm from a body surface ECG.

U.S. Pat. No. 5,297,549 to Beatty et al. (the "Beatty method"), the disclosure of which is incorporated herein by reference, discloses a method and apparatus for mapping the electrical potential distribution of a heart chamber. In the Beatty method, an intra-cardiac multielectrode mapping catheter assembly is inserted into the heart. The mapping catheter assembly includes a multi-electrode assembly with an integral reference electrode, or, preferably, a companion reference catheter. In use, the electrodes are deployed in the form of a substantially spherical assembly. The electrode assembly is spatially referenced to a point on the endocardial surface by the reference electrode or by the reference catheter which is brought into contact with the endocardial surface. The preferred electrode assembly catheter is said to carry at least 24 individual electrode sites. Additionally, the Beatty method requires knowledge of the location of each of the electrode sites on the assembly, as well as a knowledge of the cardiac geometry. These locations are preferably determined by the method of impedance plethysmography.

U.S. Pat. No. 5,311,866 to Kagan et al. discloses a heart mapping catheter assembly including an electrode assembly defining a number of electrode sites. The mapping catheter assembly also comprises a lumen to accept a reference catheter having a distal tip electrode assembly which may be used to probe the heart wall. In the preferred construction, the mapping catheter comprises a braid of insulated wires, preferably having 24 to 64 wires in the braid, each of which are used to form electrode sites. The catheter is said to be readily positionable in a heart to be used to acquire electrical activity information from a first set of non-contact electrode sites and/or a second set of in-contact electrode sites.

U.S. Pat. Nos. 5,385,146 and 5,450,846 to Goldreyer disclose a catheter that is said to be useful for mapping electrophysiological activity within the heart. The catheter body has a distal tip which is adapted for delivery of a stimulating pulse for pacing the heart or an ablative electrode for ablating tissue in contact with the tip. The catheter further comprises at least one pair of orthogonal electrodes to generate a difference signal indicative of the local cardiac electrical activity adjacent the orthogonal electrodes.

U.S. Pat. No. 5,662,108 to Budd et al. discloses a process for measuring electrophysiologic data in a heart chamber. The method involves, in part, positioning a set of active and passive electrodes into the heart; supplying current to the active electrodes, thereby generating an electric field in the heart chamber; and measuring said electric field at said passive electrode sites. In one of the disclosed embodiments, the passive electrodes are contained in an assembly positioned on an inflatable balloon of a balloon catheter. In preferred embodiments, the assembly is said to have from 60 to 64 electrodes.

Recent common practice is to use a quadrapolar catheter to map the various chambers of the heart. Moreover, a catheter is dragged around the entire chamber until enough points can together be extrapolated to provide enough information.

Thus, various methods have been proposed for increasing the speed of acquiring an electrical map of the heart. However, there remains a desire for a mapping catheter that reduces procedure time, by providing a distal electrode assembly that can expand and capture a heart chamber structure with a single sweeping moment. For example, with a slight rotation or translating motion, the assembly should be able to contact enough of the heart wall to be able to construct a complete map of the chamber. The assembly should be of a suitable shape, size and flexibility to avoid "tenting" of the heart tissue while being able to follow the motion of heart contractions.

SUMMARY OF THE INVENTION

The present invention is directed to a mapping catheter having a mapping electrode assembly that resembles a ribbon and is shaped in spiral form. The mapping electrode assembly has a support structure with shape memory and carries an array of electrodes fixed to an outer surface of the ribbon. When the mapping electrode assembly is expanded, multiple electrodes on the ribbon advantageously come into contact with tissue wall of a heart chamber, including an atrium or ventricle, for faster mapping by capturing the general chamber structure with a single sweeping movement. By providing a relatively large surface area in contact with tissue wall, the assembly provides numerous locations for recording in a mapping system. And, by slightly rotating and translating the mapping electrode assembly, a sufficient number of locations should be provided to contract a complete map of the chamber.

In one embodiment, the catheter has an elongated body and a mapping electrode assembly carried on an expander that extends the length of the catheter. The mapping electrode assembly comprises a band member configured in a spiral form around the expander such that the expander defines the longitudinal axis of the assembly. A distal end of the band member is fixed to the distal portion of the expander. A proximal end of the band member is fixed to the elongated body. As such, longitudinal movement of the expander relative to the elongated body causes the band member to change its spiral form between an expanded configuration and a contracted configuration. The band member has an outer surface on which are affixed a plurality of electrodes. The spiral form of the band member is supported by at least one strut with shape memory so the band member maintains its spiral form.

In a more detailed embodiment, the band member has an outer surface that faces outwardly along the spiral faun and the electrodes are mounted on the outer surface to contact the tissue wall. The electrodes are provided along the length of the band member which spirals at least about 360 degrees about the expander, if not about 540 degrees. Lead wires extending from the electrodes pass through folded edges or "hems" of the band member and then through a central lumen of the expander toward the control handle.

In another detailed embodiment, the expander has an exposed proximal end adapted for direct manipulation by a user to expand and contract the mapping electrode assembly. The expander can be moved longitudinally or merely rotated to achieve expansion and contraction of the assembly. In another detailed embodiment, the catheter includes a control handle with a user interface assembly that controls a puller wire to expand and contract the mapping electrode. The puller wire extends through the central lumen of the expander and its distal end is anchored to a distal portion of the expander. The user interface assembly can be adapted for linear actuation or rotational actuation by a user. In the latter instance, the user interface assembly has components that convert rotational movement into longitudinal movement.

BRIEF DESCRIPTION OF THE DRAWINGS

These and other features and advantages of the present invention will be better understood by reference to the following detailed description when considered in conjunction with the accompanying drawings. It is understood that selected structures and features have not been shown in certain drawings so as to provide better viewing of the remaining structures and features.

FIG. 6 is a side cross-sectional view of the catheter of FIG. 1, including a distal end of an intermediate section, taken along one diameter.

FIG. 6A is an end cross-sectional view of the distal end of the intermediate section of FIG. 6, taken along line A-A.

FIG. 6B is an end cross-sectional view of the distal end of the intermediate section and a proximal end of an outer sleeve of FIG. 6, taken along line B-B.

FIG. 7 is a top plan view of a proximal end and a distal end of a band member of a mapping electrode assembly in accordance with an embodiment of the present invention.

FIG. 9 is a side cross-sectional view of a distal end of a band member affixed to an expander in accordance with an embodiment of the present invention.

FIG. 9A is an end cross-sectional view of the distal end of the band member affixed to the expander of FIG. 9, taken along line A-A.

FIG. 13 is a side cross-sectional view of the distal end of the band member affixed to the expander in accordance with another embodiment of the present invention.

FIG. 13A is an end cross-sectional view of the proximal end of the band member affixed to the expander of FIG. 13, taken along line A-A.

DETAILED DESCRIPTION OF THE INVENTION

Figure 1:
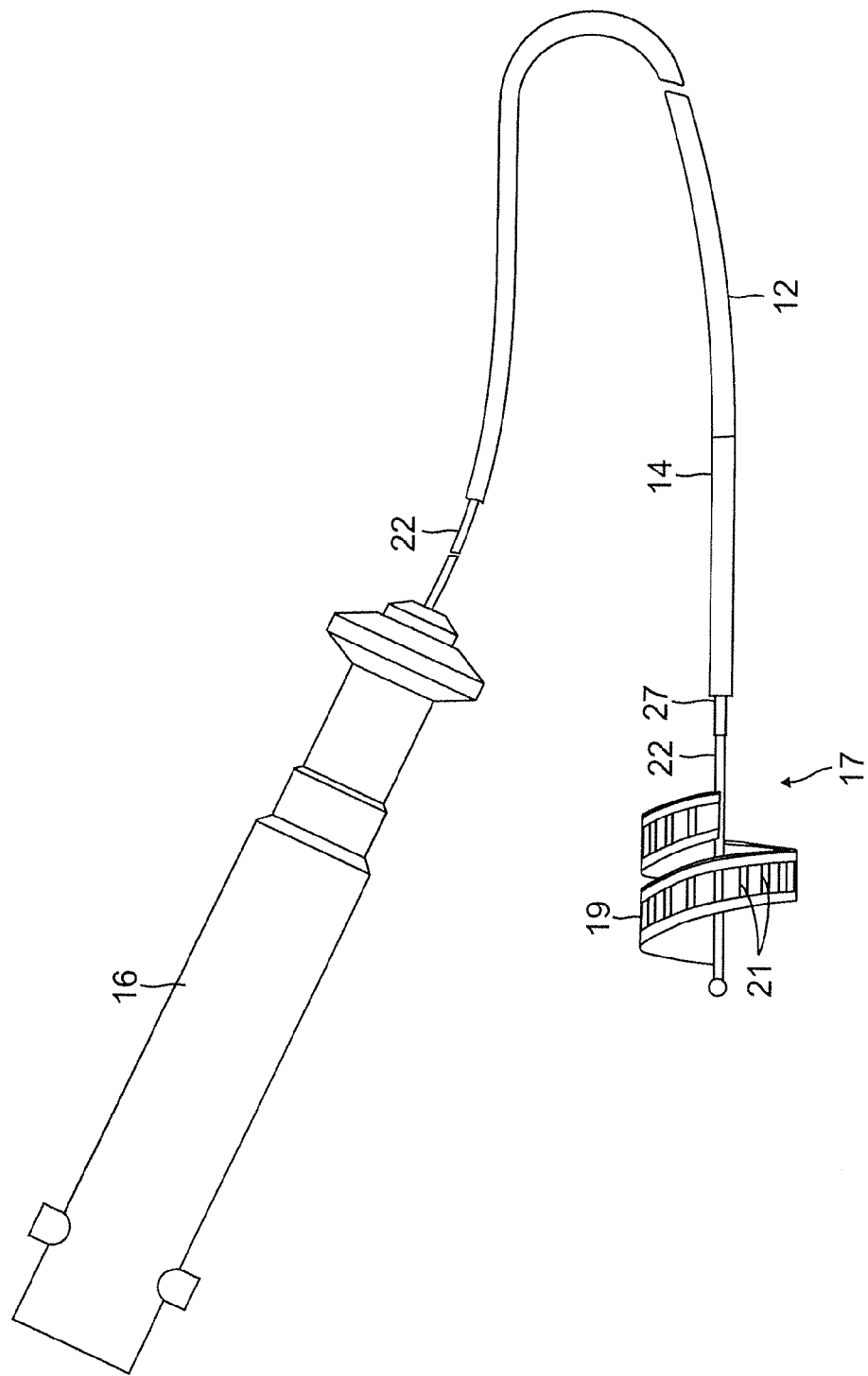
FIG. 1 is a perspective view of a catheter in accordance with an embodiment of the present invention.
Figure 2:
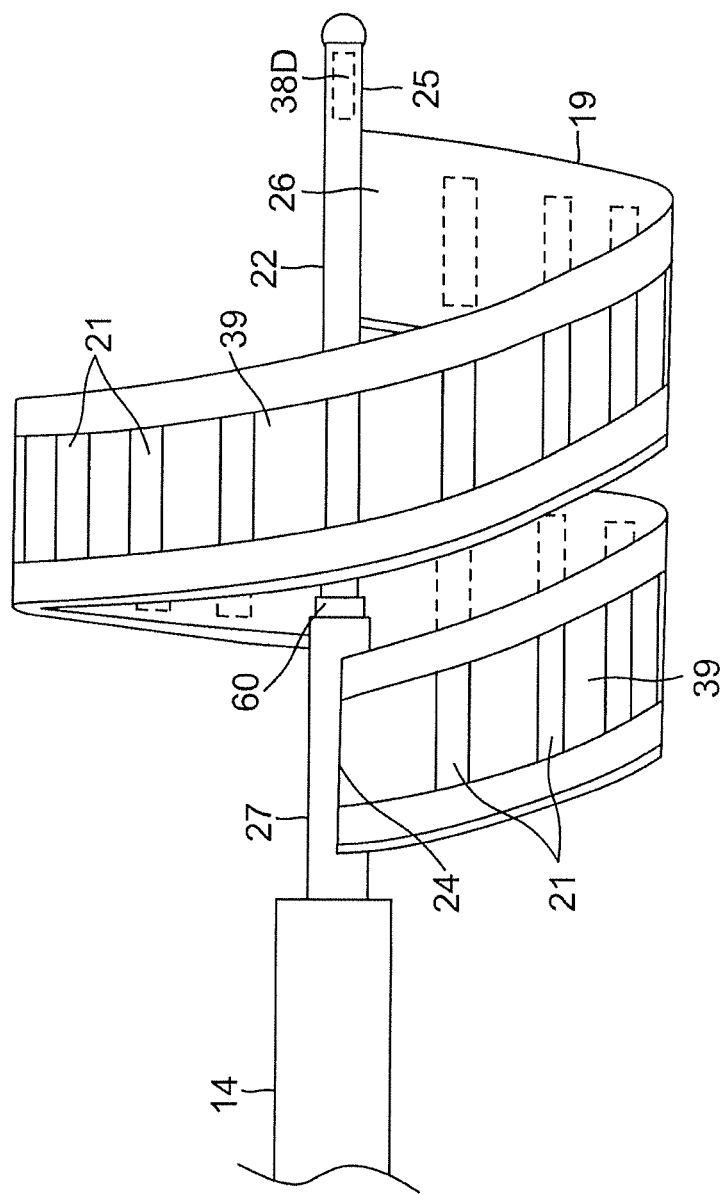
FIG. 2 is a perspective view of a mapping electrode assembly in a radially expanded or deployed configuration in accordance with an embodiment of the present invention.
Figure 3:
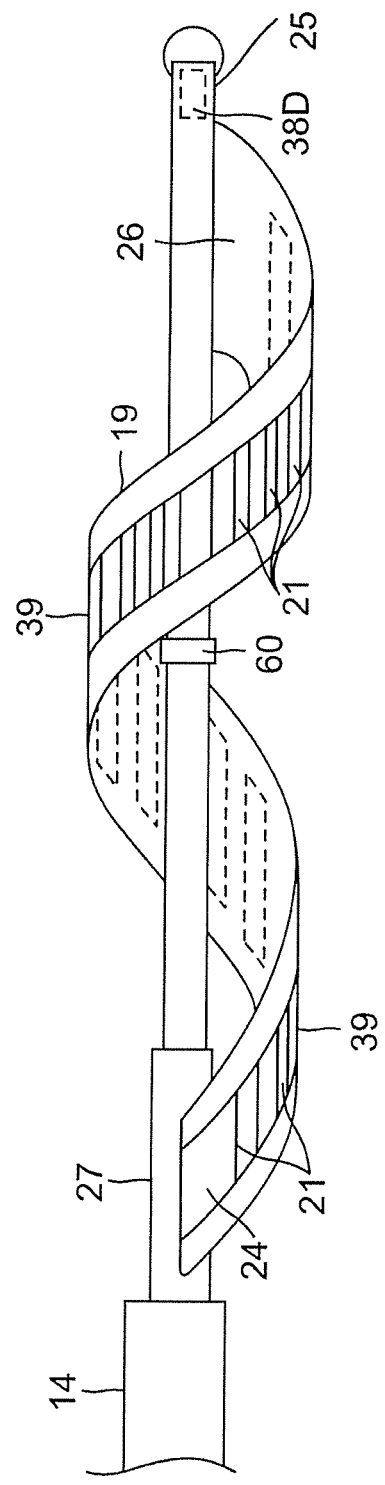
FIG. 3 is a perspective view of a mapping electrode assembly in a radially contracted configuration in accordance with an embodiment of the present invention.

As illustrated in FIGS. 1-4 the present invention includes a steerable catheter 10 with a distal tip section 17 that includes a distal mapping electrode assembly 19 carrying a plurality of electrodes 21 for multiple simultaneous contacts with wall tissue of a chamber, including a heart chamber 20, such as an atrium or ventricle. The assembly includes a flexible planar member or band resembling a "ribbon" 28 that is supported on an expander 22 in a generally spiral configuration. Advantageously, the expander can be advanced and retracted relative to the catheter to vary the spiral configuration, including radially expanding (FIG. 2) and contracting the ribbon 28 (FIG. 3). The ribbon has a proximal end 24 and a distal end 26. The proximal end 24 is fixed to an outer sleeve 27 through which the expander 22 can move longitudinally, and the distal end 26 is fixed to a distal end 25 of the expander 22. As such, the spiral configuration of the ribbon 28 is varied as the expander 22 is advanced or retracted relative to the outer sleeve by an operator. The assembly 19 may adopt the neutral or contracted configuration of FIG. 2 while the catheter is moved through a patient's vasculature toward the target location and before it is deployed in the heart chamber. When the assembly 19 reaches the target location, it is deployed and manipulated into the expanded configuration of FIGS. 3 and 4.

Figure 5A:
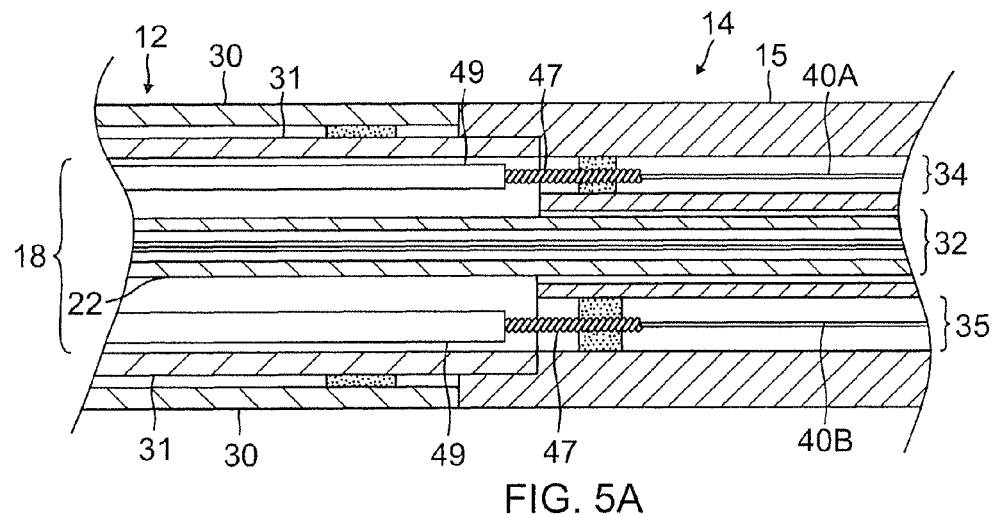
FIG. 5A is a side cross-sectional view of the catheter of FIG. 1, including a junction between a catheter body and an intermediate section, taken along one diameter.
Figure 5B:
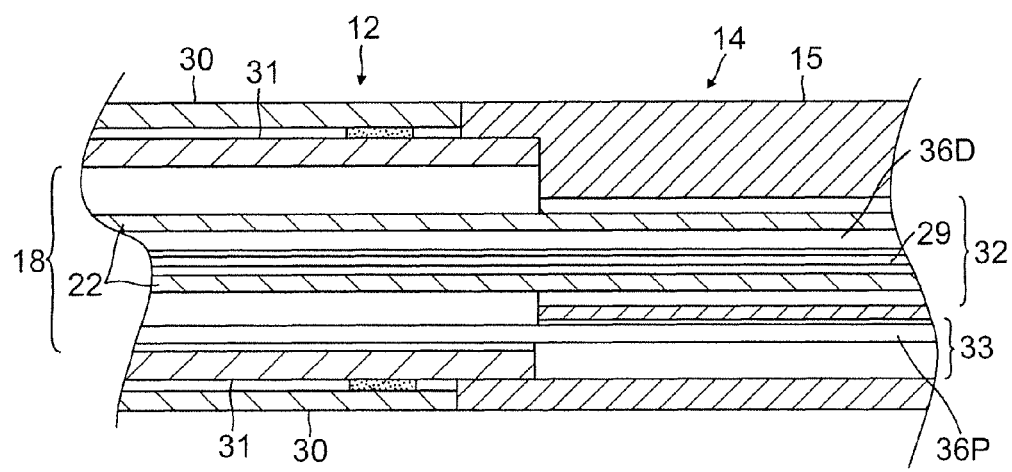
FIG. 5B is a side cross-sectional view of the catheter of FIG. 1, including a junction between a catheter body and an intermediate section, taken along another diameter.

As shown in FIGS. 5A and 5B, the catheter body 12 comprises an elongated tubular construction having a single, axial or central lumen 18, but can optionally have multiple lumens if desired. The catheter body 12 is flexible, i.e., bendable, but substantially non-compressible along its length. The catheter body 12 can be of any suitable construction and made of any suitable material. A presently preferred construction comprises an outer wall made of polyurethane or PEBAX® (polyether block amide). The outer wall comprises an imbedded braided mesh of stainless steel or the like to increase torsional stiffness of the catheter body 12 so that, when the control handle 16 is rotated, the distal end of the catheter body will rotate in a corresponding manner.

The outer diameter of the catheter body 12 is not critical, but is preferably no more than about 8 french, more preferably 7 french. Likewise the thickness of the outer wall is not critical, but is preferably thin enough so that the central lumen can accommodate a puller wire, lead wires, sensor cables and any other wires, cables or tubes. If desired, the inner surface of the outer wall is lined with a stiffening tube (not shown) to provide improved torsional stability. An example of a catheter body construction suitable for use in connection with the present invention is described and depicted in U.S. Pat. No. 6,064,905, the entire disclosure of which is incorporated herein by reference.

With further reference to FIGS. 5A and 5B the deflectable intermediate section 14 comprises a short section of tubing 15 having multiple lumens, each occupied by the various components extending through the intermediate section. In the illustrated embodiment, there are four lumens 32, 33, 34, 35 as best seen in FIG. 6C. Passing through a first and central lumen 32 are lead wires 29 for the electrode assembly 19 and a cable 36D for a distal electromagnetic position sensor 38D. Passing through a second lumen 33 is a cable 36P for a proximal electromagnetic position sensor 38P. For at least uni-directional deflection, a first puller wire 40A passes through a third, off-axis lumen 34. For bi-directional deflection, a second puller wire 40B passes through a fourth, off-axis lumen 35.

The multi-lumened tubing 15 of the intermediate section 14 is made of a suitable non-toxic material that is preferably more flexible than the catheter body 12. A suitable material is braided polyurethane or PEBAX, i.e., polyurethane or PEBAX with an embedded mesh of braided stainless steel or the like. The plurality and size of each lumen are not critical, provided there is sufficient room to house the components extending therethrough. Position of each lumen is also not critical, except the positions of the lumens 34, 35 for the puller wires 40A, 40B. The lumens 34, 35 should be off-axis, and diametrically opposite of each other for bi-directional deflection along a plane.

The useful length of the catheter, i.e., that portion that can be inserted into the body can vary as desired. Preferably the useful length ranges from about 110 cm to about 120 cm. The length of the intermediate section 14 is a relatively small portion of the useful length, and preferably ranges from about 3.5 cm to about 10 cm, more preferably from about 5 cm to about 6.5 cm.

A preferred means for attaching the catheter body 12 to the intermediate section 14 is illustrated in FIGS. 5A and 5B. The proximal end of the intermediate section 14 comprises an inner circumferential notch that receives the outer surface of the distal end of the stiffening tube 31 of the catheter body 12. The intermediate section 14 and catheter body 12 are attached by glue or the like, for example, polyurethane. If desired, a spacer (not shown) can be provided within the catheter body 12 between the distal end of the stiffening tube 31 and the proximal end of the intermediate section 14 to provide a transition in flexibility at the junction of the catheter body 12 and the intermediate section, which allows the junction to bend smoothly without folding or kinking. An example of such a spacer is described in more detail in U.S. Pat. No. 5,964,757, the disclosure of which is incorporated herein by reference.

As illustrated in FIGS. 6 and 6A, a deflection puller wire 40A extends through the central lumen 18 of the catheter body 12 and into the third lumen 34 of the intermediate section 14. Another deflection puller wire 40B extends through the central lumen 18 and into the fourth lumen 35 of the intermediate section 14. The distal ends of the deflection puller wires are anchored to the wall of the tubing 15 near the distal end of the intermediate section 14 by means of T-anchors 81. In the intermediate section 14, each deflection puller wire extends through a plastic, e.g., Teflon®, sheath 83, which prevents the deflection puller wires from cutting into the wall of the tubing 15 of the intermediate section 14 when the intermediate section 14 is deflected.

As shown in FIG. 5A, compression coils 47 in surrounding relation to the deflection puller wires extend from the proximal end of the catheter body 12 to about the proximal end of the intermediate section 14. The compression coils 47 are made of any suitable metal, e.g., stainless steel. The compression coils are tightly wound on itself to provide flexibility, i.e., bending, but to resist compression. The inner diameter of the compression coils is preferably slightly larger than the diameter of the puller wires. A Teflon® coating on the puller wires allows them to slide freely within the compression coils. The outer surface of the compression coils is covered by a flexible, non-conductive sheath 49 to prevent contact between the compression coils and other components, such as lead wires and cables, etc. A non-conductive sheath can be made of polyimide tubing.

The compression coils are anchored at their proximal ends to the proximal end of the stiffening tube 20 in the catheter body 12 by glue joint (not shown) and at its distal end near the proximal end of the intermediate section 14 in the lumen 34, 35 by glue joints (FIG. 5A).

As for the distal tip section 17, the spiral-shaped ribbon electrode assembly 19 is mounted to the distal end of the intermediate section 14. As shown in FIG. 6, the ribbon 28 extends around the expander 22 between about 180 and 720 degrees, preferably at least 360 degrees, and more preferably about 540 degrees. The ribbon has an outer surface 39 that consistently faces outwardly from the expander 22. Elongated and resembling a tubular shaft or rod, the expander forms the central longitudinal axis of the electrode assembly 19.

The ribbon 28 may be constructed of any suitable material, including PEBAX. The exposed length of the ribbon between its distal and proximal ends is about 10 and 25 cm, and preferably about 15 mm, and more preferably about 20 mm. The ribbon has a width about 2 and 10 mm, and preferably about 5 and 8 mm. It is understood that the ribbon may be constructed as a solid member, a woven member or a web member, provided the structure is sufficiently rigid yet flexible to support the electrodes and hold the generally spiral form in the expanded and contracted configurations.

Supporting the ribbon 28 on the expander 22 and enabling the ribbon to elastically and flexibly maintain its shape are two shape-memory struts 42A, 42B, each of which extends along a lengthwise edge 43 of the ribbon and is secured and protected by a peripheral length edge portion of the ribbon (or "hem") 45 that is folded along edge 43. Extending widthwise between the folded edge portions are a plurality of elongated electrodes 21, ranging between about 10 and 50, and more preferably about 20 and 41. In the illustrated embodiment, they are evenly spaced, span nearly the length of the ribbon and are generally parallel with the expander and longitudinal axis of the catheter. They are affixed to the outer surface in a suitable manner, including, e.g., adhesives, so that they can readily contact tissue when the assembly is expanded (see FIG. 4).

Figure 8:
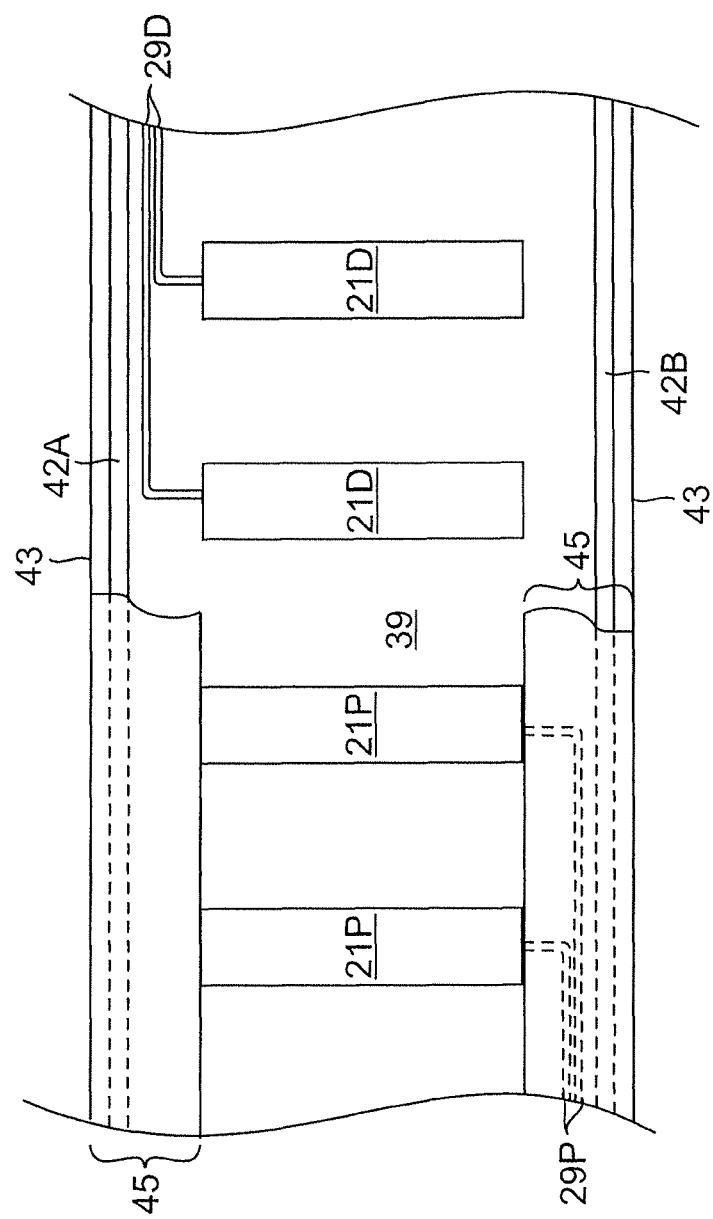
FIG. 8 is a top plan view of a mid-section a band member of a mapping electrode assembly in accordance with an embodiment of the present invention.

Each electrode 21 is connected to a respective lead wire 29. In the illustrated embodiment of FIGS. 7 and 8, lead wires 29D for a distal portion of the electrodes 21D travel alongside one lengthwise edge 43 of the ribbon 28 and lead wires 29P for a proximal portion of the electrodes 21P travel alongside the other lengthwise edge 43 of the ribbon. The lead wires are also covered and protected by the hem 45 of the ribbon inward of the nitinol struts 42A, 42B.

The distal end 26 of the ribbon 28 is fixed to a distal end portion of the expander 22. As illustrated in FIGS. 9, 9A, an axial opening or slot 48D is formed in the expander 22 near its distal end. The distal end 26 of the ribbon is inserted in the slot which is sized to fit the width of the ribbon but holds distal anchors 44D formed in the distal end of each strut 42A, 42B. In the illustrated embodiment, the distal end of each strut is bent at an angle (e.g., about 90 degrees) to form a hook that latches to distal and proximal sides of the slot 48D in the expander 22. The distal widthwise edge portion 50 of ribbon is tucked in the slot 48D and the anchors 44D are positioned in lumen 23 of the expander 22. Lead wires 29D for the distal portion of the electrodes 21D (only one shown for clarity) extend into the lumen 23 of the expander 22 where they pass proximally toward the control handle 16. The distal end of the ribbon 26 (along with the distal strut anchors 44D) is fixed and sealed in the slot 48D with suitable material, e.g., epoxy.

Housed in the distal end of the expander 22 is the distal location sensor 38D. In the illustrated embodiment, the distal location sensor is distal of the distal end 26 of the ribbon 28 however it can be at another location as appropriate. Cable 36D for the distal location sensor 38D also passes through the lumen 23 of the expander 22 toward the control handle 16. A distal tip 51 of the expander 22 is sealed with suitable material, e.g., epoxy to form an atraumatic end.

Figure 10:
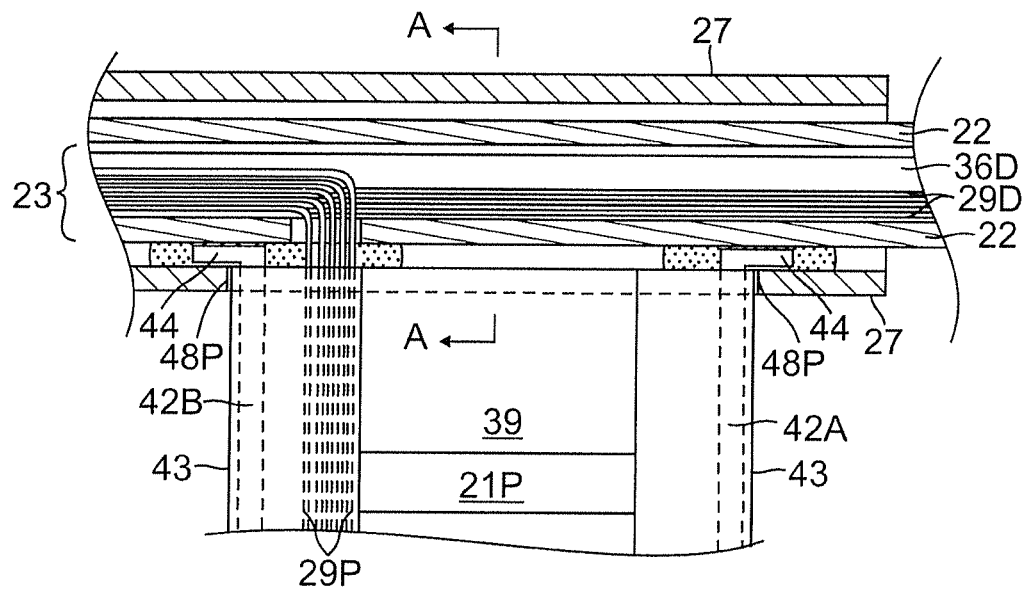
FIG. 10 is a side cross-sectional view of the proximal end of the band member affixed to the expander in accordance with an embodiment of the present invention.
Figure 10A:
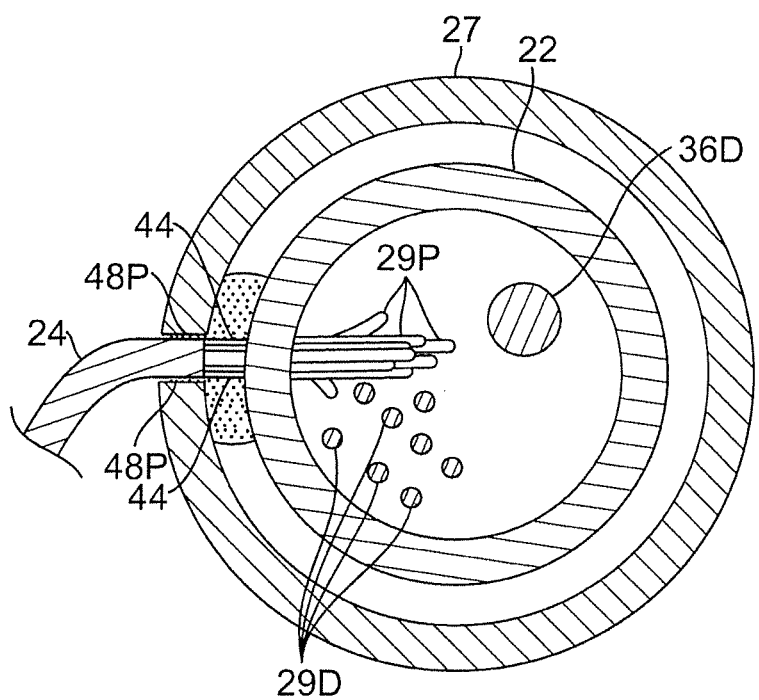
FIG. 10A is an end cross-sectional view of the proximal end of the band member affixed to the expander of FIG. 10, taken along line A-A.

The proximal end 24 of the ribbon 28 is fixed to the outer sleeve 29 near its distal end. As illustrated in FIGS. 6, 10 and 10A, an opening axial slot 48P is formed in the outer sleeve 27. The proximal end 24 of the ribbon 28 is inserted in the slot 48P which is sized to fit the width of the ribbon but holds anchors 44P formed in the proximal end of each strut 44A, 44B. In the illustrated embodiment, the proximal end of each strut is bent at an angle (e.g., about 90 degrees) to form a hook that latches to distal and proximal sides of the slot in the outer sleeve 27. The proximal widthwise edge portion 50P of ribbon is tucked in the slot 48P and the anchors 44P are positioned in a gap 52 between the expander 22 and the outer sleeve 27. Lead wires 29P for the proximal portion of the electrodes 21P extend into the lumen 23 of the expander 22 where they pass proximally toward the control handle 16 (along with the lead wires 29D for the distal portion of the electrodes 21D and the cable 36D for the distal location sensor 38D). The proximal end 24 of the ribbon (along with the proximal strut anchors 44P) is fixed and sealed in the slot 48P with suitable material, e.g., epoxy.

Housed in the distal end of tubing 15 of the intermediate deflection section 14 is the proximal location sensor 38P. In the illustrated embodiment of FIG. 6A, the proximal location sensor 38P is proximal of the proximal end of the outer sleeve 27 however it can be at another location as appropriate. Cable 36P for the proximal location sensor 38P also passes through the lumen 23 of the expander 22 toward the control handle 16.

The coordinates of the distal sensor 38D, relative to those of the proximal sensor 38P, are determined and taken together with other known information pertaining to the curvature/position of the ribbon 28 of the electrode assembly 19. This information is used to find the positions of the electrodes 21 mounted on the ribbon. However, it is understood that other location sensors may be used, including Single-Axis-Sensors (SAS), such as those described in U.S. application Ser. No. 12/982,765, filed Dec. 30, 2010, entitled CATHETER WITH SINGLE AXIAL SENSORS, the entire disclosure of which is hereby incorporated by reference.

Figure 11:
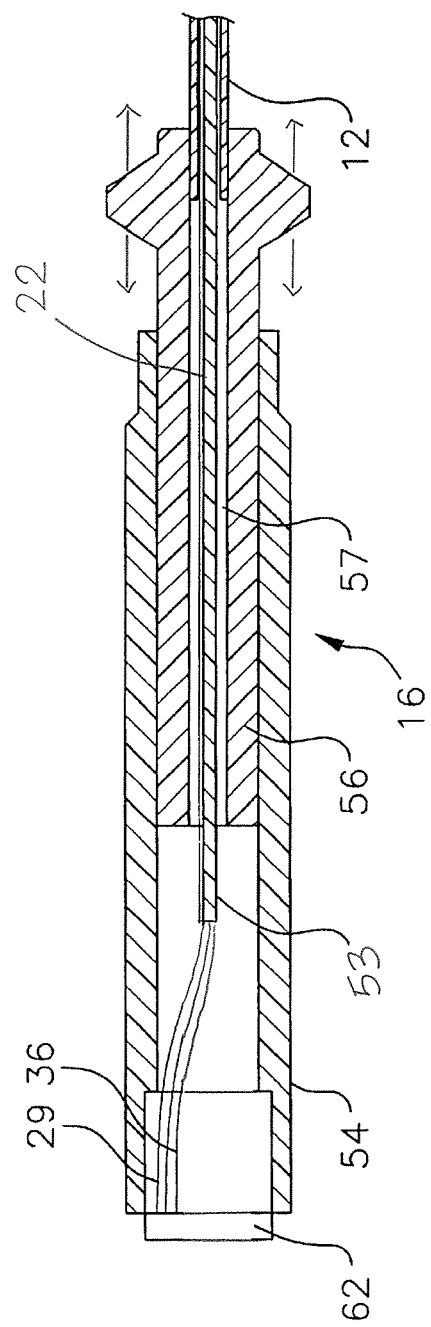
FIG. 11 is a side cross-sectional view of a control handle in accordance with an embodiment of the present invention.

As shown in the depicted embodiment, the expander 22 is generally coaxial with the intermediate deflection section 14 and the catheter body 12. As shown in FIG. 11, the expander 22 has a proximal end 53 attached to the control handle 16, as described further below, so that the expander can be moved longitudinally relative to the catheter body 12 to thereby expand and contract the electrode assembly 19. The expander 22 comprises a material sufficiently rigid to achieve this function. In a preferred embodiment, the expander 22 comprises braided polyimide tubing, i.e., tubing having inner and outer layers of polyimide with a braided stainless steel mesh therebetween, as is generally known in the art.

Longitudinal movement of the expander 22 relative to the catheter body 12, which results in expansion of the electrode assembly 18, is accomplished by manipulation of the control handle 16. As shown in FIG. 11, the control handle 16 comprises a generally-hollow handle housing 54 and a piston (or thumb control) 56 slidably mounted within the distal end of the handle housing. The proximal end of the catheter body 12 is fixedly attached to the distal end of the piston 56 by a shrink sleeve (not shown), as is generally known in the art, or by any other suitable method. Within the control handle 16, the proximal end of the expander 22 extends through a passage 57 in the piston 56 and is secured and fixed to the handle housing 54. The expander 22 is fixedly attached to the handle housing 54 by any suitable method, preferably with polyurethane glue or the like.

In one embodiment, the piston 56 is approximately about 2 inches long, and the support tube 58 and expander 22 are attached to the handle housing 54 at a position about 0.5 inch distal to the proximal end of the handle and about 1 inch proximal to the proximal end of the piston in the neutral position. The piston is in the neutral position (with the distal and proximal ends of the ribbon at a maximum separation) when the electrode assembly 19 is more tightly coiled around the expander, i.e., not expanded. And by moving the piston 56 distally, the catheter body 12 and consequently the intermediate section 14 and outer sleeve 27 and the proximal end 24 of the ribbon 28 is moved distally (decreasing the separation between the proximal and distal ends 24, 26 of the ribbon) to radially expand the ribbon (FIG. 2). A stopper 60 can be provided on the expander 22 to limit the minimum separation permitted between the ends 24, 26 of the ribbon by abutting against the distal end of the outer sleeve 27. The lead wires 29D, 29P and sensor cables 36D, 36P extend through the lumen 23 of the expander 22 and past the proximal end 53 of the expander where they are attached to suitable connector(s) 62 at the proximal end of the handle housing.

Figure 12:
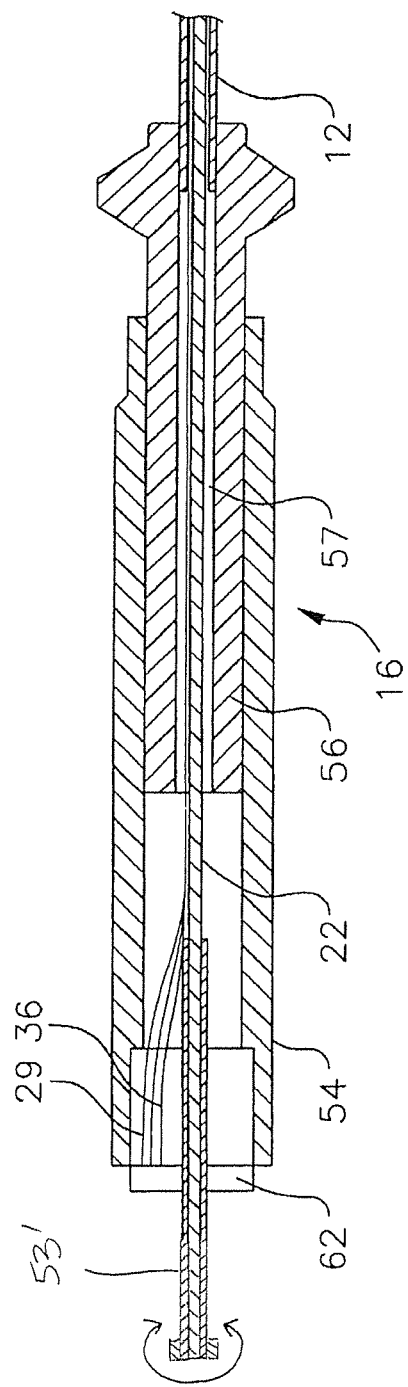
FIG. 12 is a side cross-sectional view of a control handle in accordance with another embodiment of the present invention.

In an alternate embodiment of FIG. 12, the expander 22 passes through the control handle 16 and has an exposed proximal end 53' proximal of the control handle 16. In this instance, the expander can be made of a material with sufficient torsional stiffness such that when the exposed proximal end 53' is rotated by a user, the distal end 25 of the expander rotates in a corresponding manner. As such, a user can radially expand the ribbon and contract it by merely rotating the exposed proximal end of the expander.

Figure 14:
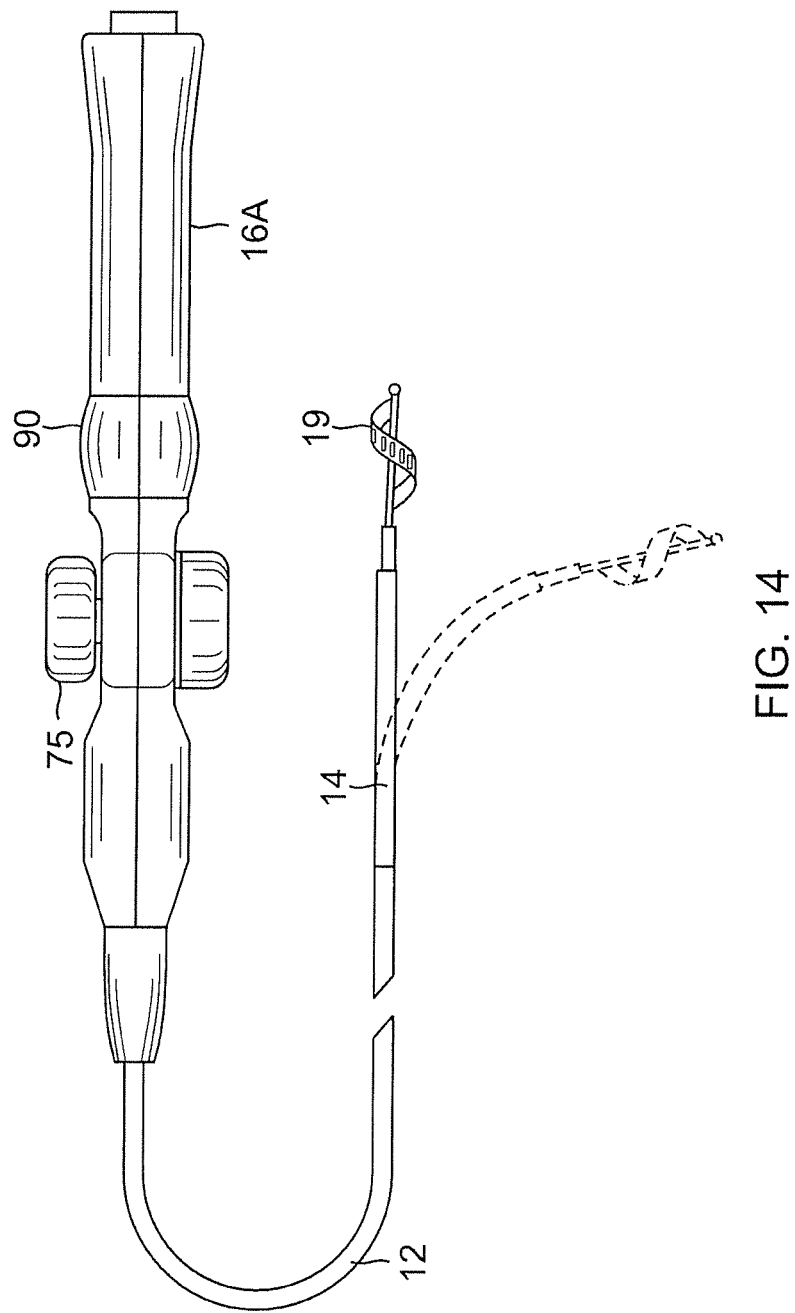
FIG. 14 is a top plan view of a catheter in accordance with another embodiment of the present invention.
Figure 15:
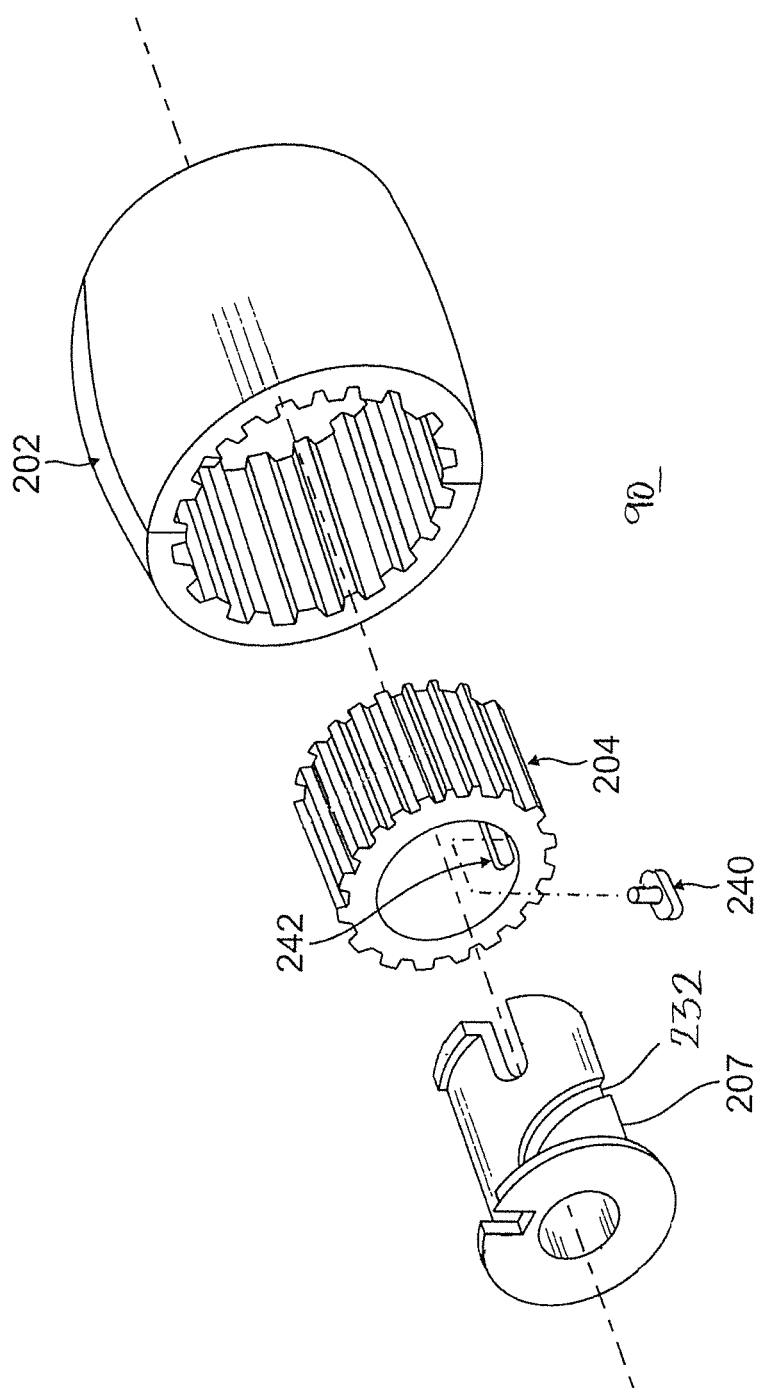
FIG. 15 is a perspective view of a control handle rotational interface assembly in accordance with one embodiment of the present invention.
Figure 16:
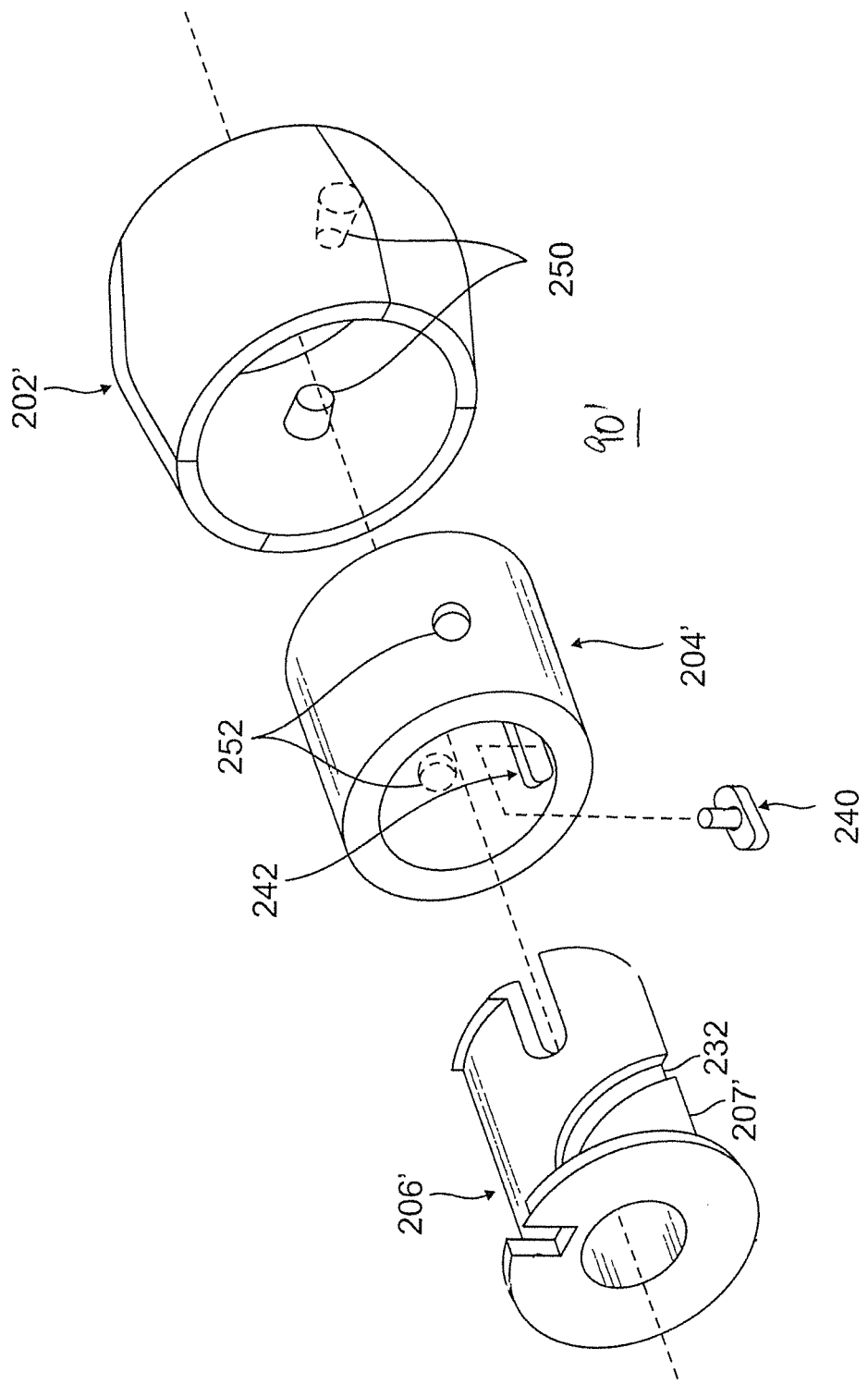
FIG. 16 is a perspective view of a control handle rotational interface assembly in accordance with another embodiment of the present invention.

In another alternate embodiment as illustrated in FIGS. 13 and 13A, longitudinal movement of the expander can be accomplished by a third puller wire 80 extending through the lumen 23 of the expander 22. The distal end of the puller wire is anchored in any suitable manner, for example, a T-bar 82, at or near the distal end of the expander. Manipulation of the third puller wire 80 (and any other puller wires such as puller wires 40A, 40B, for uni- or bi-deflection of the intermediate section 14) can be accomplished by suitable control handles, including the control handles disclosed in U.S. Patent Applications entitled CATHETER WITH MULTI-FUNCTIONAL HANDLE HAVING LINEAR MECHANISM, Ser. No. 12/550,204, filed Aug. 28, 2009 and CATHETER WITH MULTI-FUNCTIONAL CONTROL HANDLE HAVING ROTATIONAL MECHANISM, Ser. No. 12/550,307, filed Aug. 28, 2009, the entire disclosures of which are incorporated herein by reference. The control handles therein employ components and assemblies that convert rotational motion into translational motion, including a rotational user interface that result in longitudinal motion of a follower to which a puller wire is attached. As illustrated in FIG. 14, a control handle 16A has a deflection control knob 75 and a rotational assembly 90. The deflection control knob 75 allows control of deflection of intermediate section 14 and the rotational assembly 90 allows control of the expansion and contraction of the electrode assembly 19. In the illustrated embodiment of FIG. 15, the rotational assembly 90 includes an outer rotational member 202, an inner gear 204 with a guiding slot 242 and a cylindrical member 207 having a track 232 in which a follower 240 rides as guided by the slot 242. Rotation of the member 202 rotates the gear 204 which in turn slides the follower 240 along the track by means of the slot 242. As the follower sides in the track, the puller wire attached thereto is moved longitudinally relative to the control handle to actuate a component, including expansion and contraction of the electrode assembly. FIG. 16 illustrates another embodiment of a rotational assembly 90' operating in a similar manner, except with a gearless inner member 204' is rotationally coupled to the outer rotational member 202' by pins 250 received in apertures 252.

Figure 17:
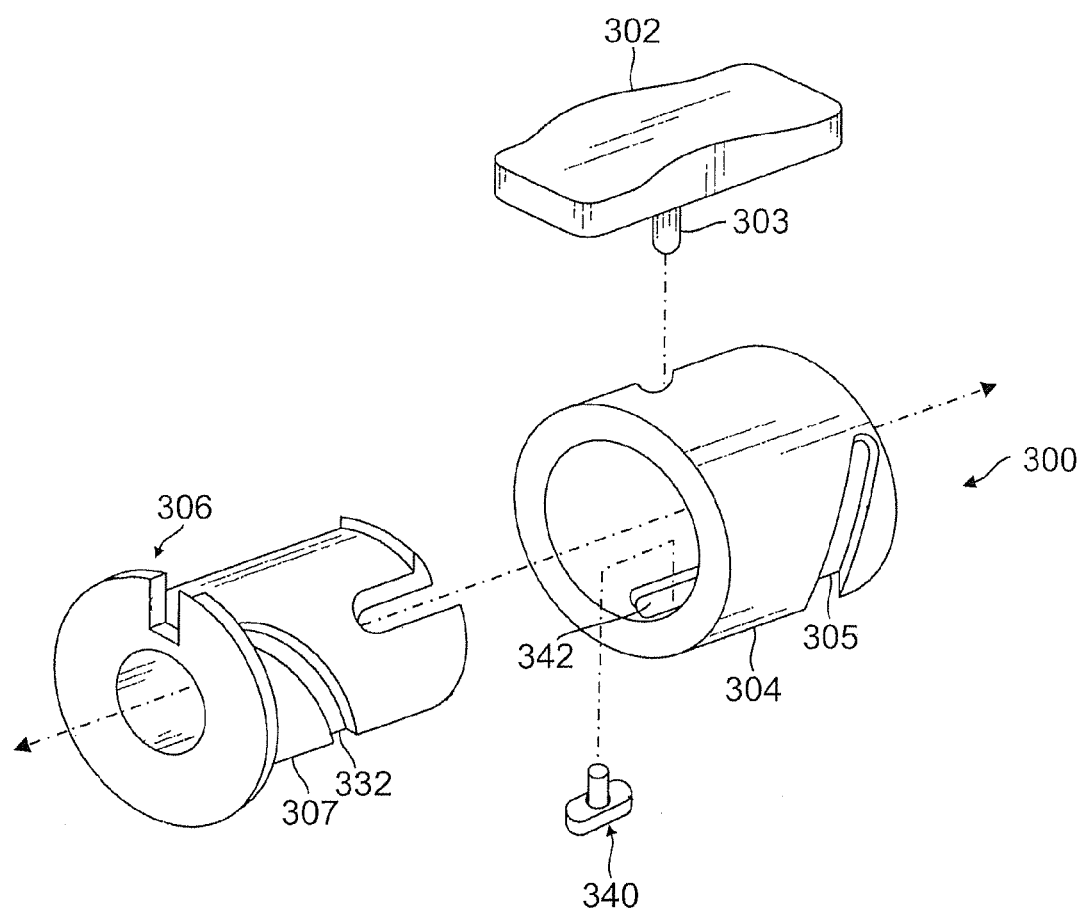
FIG. 17 is a perspective view of a control handle linear interface assembly in accordance with another embodiment of the present invention.

FIG. 17 illustrates yet another embodiment of a suitable rotational assembly. A linear interface 302 rotates an inner cylindrical member by a pin 303. The control handle housing has an axial slot (not shown) that guides movement of the interface 302 along the longitudinal axis of the control handle. As the pin 303 moves longitudinally, it slides in track 305 and rotates an outer cylindrical member 304 which has an axial guiding slot 342 in which sits a follower 340 that slides along a track 332 formed in an inner cylindrical member. As the follower moves in the track, the puller wire attached thereto moves longitudinally relative to the control handle to actuate a component, including the electrode assembly for expansion and contraction.

Each location sensor 38P and 38D is connected to a corresponding sensor cable 36P and 36D that extend through the expander to the control handle 16 and out the proximal end of the control handle within an umbilical cord (not shown) to a sensor control module (not shown) that houses a circuit board (not shown). Alternatively, the circuit board can be housed within the control handle 16, for example, as described in U.S. Pat. No. 6,024,739, the disclosure of which is incorporated herein by reference. Each sensor cable comprises multiple wires encased within a plastic covered sheath. In the sensor control module, the wires of the sensor cable are connected to the circuit board. The circuit board amplifies the signal received from the corresponding location sensor and transmits it to a computer in a form understandable by the computer by means of the sensor connector at the proximal end of the sensor control module. Also, because the catheter is designed for single use only, the circuit board preferably contains an EPROM chip that shuts down the circuit board approximately twenty-four hours after the catheter has been used. This prevents the catheter, or at least the location sensor, from being used twice.

Figure 4:
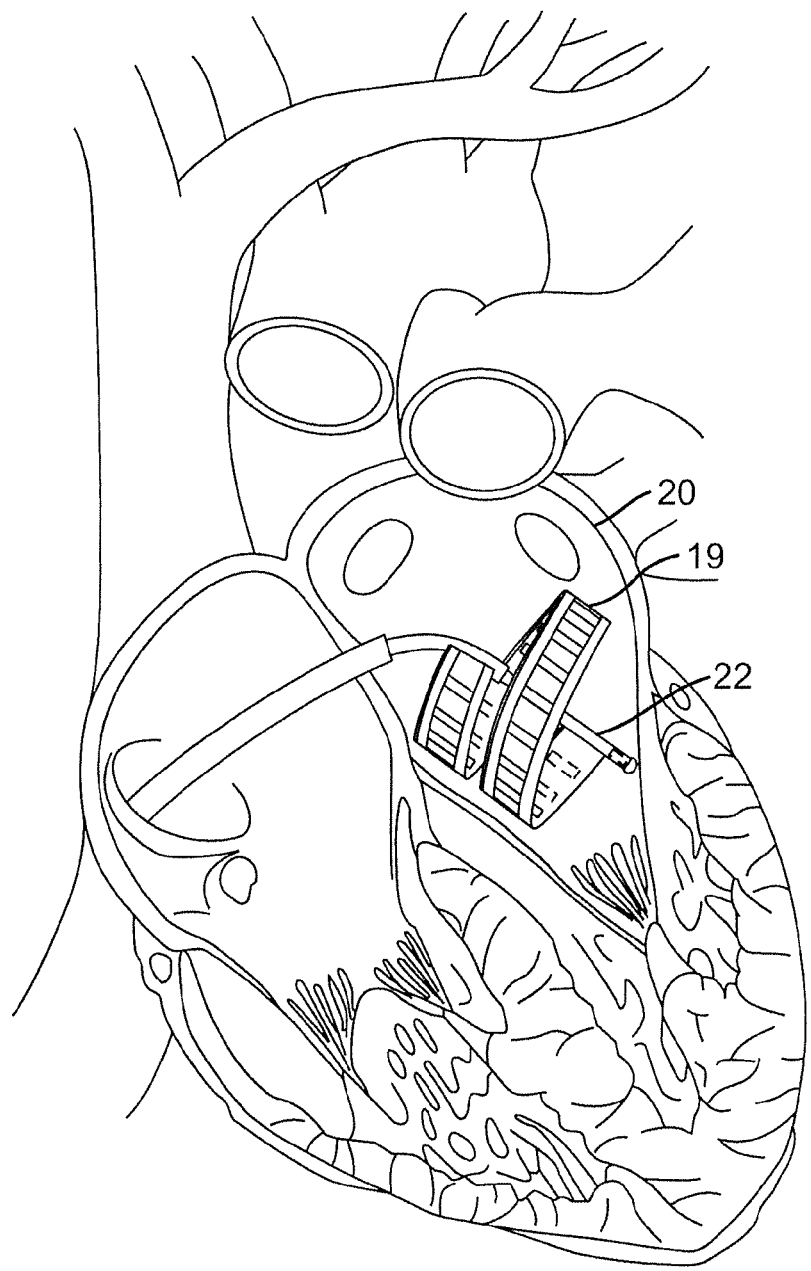
FIG. 4 is a schematic sectional view of a heart showing insertion of a catheter of the present invention into the left atrium, in accordance with an embodiment of the present invention.

To use the catheter of the invention, an electrophysiologist introduces a guiding sheath, into the patient, as is generally known in the art. A suitable guiding sheath for use in connection with the inventive catheter is the PREFACE™. Braided Guiding Sheath (commercially available from Biosense Webster, Inc., Diamond Bar, Calif.). The catheter is introduced through the guiding sheath. The guiding sheath covers the electrode assembly 19 internally in a collapsed or contracted position so that the entire catheter can be passed down a vein or artery to a desired location. Once the distal end of the catheter reaches the desired location, the guiding sheath is withdrawn. The expander 22 is then manipulated so that the ribbon 28 of the electrode assembly 18 flexes outwardly into an expanded arrangement (FIG. 4). In such an arrangement, the electrodes 21 on the ribbon contact the tissue of the heart. As will be recognized by one skilled in the art, the electrode assembly 19 can be fully or partially expanded in a variety of configurations depending on the configuration of the region of the heart being mapped.

The catheter of the present invention increases the speed of acquiring an electrical map of the heart by providing an electrode assembly that can expand and capture a heart chamber structure with a single sweeping moment. For example, with a slight rotation or translating motion, the assembly should be able to contact enough of the heart wall to be able to construct a complete map of the chamber. The assembly should be of a suitable shape, size and flexibility to avoid "tenting" of the heart tissue while being able to follow the motion of heart contractions.

Using the electrodes on the ribbon of the electrode assembly 18 in combination with the distal end proximal location sensors 38D, 38P, the electrophysiologist can map local activation time, which can guide the electrophysiologist in providing therapy to the patient. The catheter can include one or more reference ring electrodes mounted on the catheter body 12, or one or more reference electrodes can be placed outside the body of the patient. By using the inventive catheter with the multiple electrodes 21 on the electrode assembly 19, the electrophysiologist can obtain a true anatomy of the heart by measuring multiple points simultaneously, allowing him to map the heart more quickly.

The preceding description has been presented with reference to presently preferred embodiments of the invention. Workers skilled in the art and technology to which this invention pertains will appreciate that alterations and changes in the described structure may be practiced without meaningfully departing from the principal, spirit and scope of this invention. Any feature or structure disclosed in one embodiment may be incorporated in lieu of or in addition to other features of any other embodiments, as needed or appropriate. As understood by one of ordinary skill in the art, the drawings are not necessarily to scale, and for purposes of clarity, the plurality of lead wires illustrated are not intended to necessarily represent the plurality of electrodes employed in the catheter. Accordingly, the foregoing description should not be read as pertaining only to the precise structures described and illustrated in the accompanying drawings, but rather should be read consistent with and as support to the following claims which are to have their fullest and fair scope.

What is claimed is:

1. A catheter, comprising:
    an elongated body;
    an elongated expander extending through the elongated body, and
    a distal electrode assembly distal a distal end of the elongated body, including:
        a band member configured in a spiral form about the expander, the band member having a length between a distal end and a proximal end, the distal end being fixed to the expander, the proximal end being in a fixed relationship with the elongated body;
        a plurality of electrodes carried on the band member; and
        two support members with shape memory, each support member extending along a respective lengthwise edge of the band member to flexibly support the spiral form;
    wherein the expander is longitudinally movable relative to the elongated body to vary the spiral form of the band member.

2. A catheter of claim 1, wherein the band member has an outer surface that faces outwardly along the spiral form and the electrodes are mounted on the outer surface.

3. A catheter of claim 1, wherein the expander is longitudinally movable relative to the elongated body to vary the spiral form of the band member between a radially expanded configuration and a radially contracted configuration.

4. A catheter of claim 1, wherein the electrodes are elongated and generally parallel to the expander.

5. A catheter of claim 1, wherein the expander has an exposed proximal end adapted for direct manipulation by a user for longitudinal movement relative to the elongated body.

6. A catheter of claim 1, further comprising:
    a control handle with a user interface assembly, and a puller wire extending through the elongated body and having a distal end anchored in the expander and a proximal end responsive to the user interface assembly for longitudinal movement relative to the elongated body.

7. A catheter of claim 6, wherein the user interface assembly includes an interface configured for linear motion relative to a control handle housing.

8. A catheter of claim 6, wherein the user interface assembly includes an interface configured for rotational movement relative to a control handle housing.

9. A catheter, comprising:
    a catheter body;
    a deflectable intermediate section distal of the catheter body;
    an elongated expander extending through the catheter body and the intermediate section, and
    a distal electrode assembly distal a distal end of the intermediate section, including:
        a band member configured in a spiral form about the expander, the band member having a length between a distal end and a proximal end, the distal end being fixed to the expander, the proximal end being fixed at or near a distal end of the intermediate section;
        a plurality of electrodes carried on the band member; and
        two support members with shape memory, each support member extending along a respective lengthwise edge of the band member to flexibly support the spiral form;
    wherein the expander is longitudinally movable relative to the elongated body to vary the spiral form of the band member between a radially expanded configuration and a radially contracted configuration.

10. A catheter of claim 9, wherein the band member has an outer surface that faces outwardly along the spiral form and the electrodes are mounted on the outer surface.

11. A catheter of claim 9, wherein the expander is longitudinally movable relative to the catheter body to vary a separation distance between the proximal and distal ends of the band member.

12. A catheter of claim 9, wherein the electrodes are elongated and generally parallel to the expander.

13. A catheter of claim 9, wherein the expander is adapted for longitudinal movement relative to the catheter body by direct manipulation by a user of a proximal end of the expander.

14. A catheter of claim 9, further comprising:
a control handle with a user interface assembly, and
a puller wire extending through the catheter body and having a distal end anchored in the expander and a proximal end responsive to the user interface assembly for longitudinal movement relative to the catheter body and the intermediate section.

15. A catheter of claim 14, wherein the user interface assembly includes an interface configured for linear motion relative to a control handle housing.

16. A catheter of claim 14, wherein the user interface assembly includes an interface configured for rotational movement relative to a control handle housing.

17. A catheter of claim 9, further comprising a distal position sensor housed at or near a distal end of the expander, and a proximal position sensor positioned proximal of the distal position sensor.

* * * * *